(12) United States Patent
Kisailus et al.

(10) Patent No.: US 8,541,015 B1
(45) Date of Patent: Sep. 24, 2013

(54) THREE-DIMENSIONAL BIOLOGICAL SCAFFOLD AND METHOD OF MAKING THE SAME

(75) Inventors: David Kisailus, Riverside, CA (US); Alan J. Jacobsen, Santa Monica, CA (US); Chaoyin Zhou, Chino, CA (US)

(73) Assignee: HRL Laboratories, LLC, Malibu, CA (US)

( * ) Notice: Subject to any disclaimer, the term of this patent is extended or adjusted under 35 U.S.C. 154(b) by 0 days.

(21) Appl. No.: 13/560,932

(22) Filed: Jul. 27, 2012

Related U.S. Application Data (62) Division of application No. 12/109,262, filed on Apr. 24, 2008, now Pat. No. 8,287,895.

(51) Int. Cl.
*A61F 2/00* (2006.01)
*C12N 11/08* (2006.01)
*C12N 5/07* (2010.01)
*C12M 1/00* (2006.01)

(52) U.S. Cl.
USPC ........... 424/423; 435/180; 435/325; 435/395; 435/283.1

(58) Field of Classification Search
None
See application file for complete search history.

(56) References Cited

U.S. PATENT DOCUMENTS

| | | | |
|---|---|---|---|
| 4,219,597 A | 8/1980 | Maistre | |
| 4,400,421 A | 8/1983 | Stover | |
| 4,568,595 A | 2/1986 | Morris | |
| 4,575,330 A | 3/1986 | Hull | |
| 4,722,089 A | 1/1988 | Botez et al. | |
| 5,006,937 A | 4/1991 | Nonoshita et al. | |
| 5,185,297 A | 2/1993 | Park et al. | |
| 5,265,185 A | 11/1993 | Ashley | |
| 5,394,490 A | 2/1995 | Kato et al. | |
| 5,401,694 A | 3/1995 | Gesing et al. | |
| 5,402,514 A | 3/1995 | Booth et al. | |
| 5,932,397 A | 8/1999 | Mustacich | |
| 6,176,874 B1 | 1/2001 | Vacanti et al. | |
| 6,274,288 B1 | 8/2001 | Kewitsch et al. | |
| 6,341,190 B1 | 1/2002 | Summersgill et al. | |
| 6,379,962 B1 | 4/2002 | Holy et al. | |
| 6,387,593 B1 | 5/2002 | Kewitsch et al. | |
| 6,472,210 B1 | 10/2002 | Holy et al. | |
| 6,500,401 B2 | 12/2002 | Reznek et al. | |
| 6,510,260 B2 | 1/2003 | Chen et al. | |
| 6,592,787 B2 | 7/2003 | Pickrell et al. | |
| 6,631,231 B2 | 10/2003 | Mizuuchi et al. | |
| 6,650,817 B2 | 11/2003 | Murali | |
| 6,660,192 B1 | 12/2003 | Kim et al. | |
| 6,670,039 B1 | 12/2003 | Nagle et al. | |
| 6,684,007 B2 | 1/2004 | Yoshimura et al. | |
| 6,823,116 B2 | 11/2004 | Inui et al. | |
| 6,862,393 B2 | 3/2005 | Nashimoto | |
| 6,870,976 B2 | 3/2005 | Chen et al. | |
| 6,875,442 B2 | 4/2005 | Holy et al. | |
| 6,879,757 B1 | 4/2005 | Zhou et al. | |
| 6,887,809 B1 | 5/2005 | Adler | |
| 6,898,362 B2 | 5/2005 | Forbes et al. | |
| 6,925,233 B2 | 8/2005 | Inui et al. | |
| 6,932,880 B2 | 8/2005 | Inui et al. | |
| 6,941,888 B2 | 9/2005 | Barsoum | |
| 6,952,504 B2 | 10/2005 | Bi et al. | |
| 6,993,235 B2 | 1/2006 | Takagi et al. | |
| 6,993,406 B1 | 1/2006 | Cesarano, III et al. | |
| 7,006,747 B2 | 2/2006 | Escuti et al. | |
| 7,014,661 B2 | 3/2006 | Blunn et al. | |
| 7,020,374 B2 | 3/2006 | Talin et al. | |
| 7,022,522 B2 | 4/2006 | Guan et al. | |
| 7,024,093 B2 | 4/2006 | Shelnut et al. | |
| 7,085,467 B2 | 8/2006 | Ikemoto et al. | |
| 7,209,622 B2 | 4/2007 | Hoshi et al. | |
| 7,382,959 B1 | 6/2008 | Jacobsen | |
| 7,421,159 B2 | 9/2008 | Yang et al. | |
| 7,531,120 B2 | 5/2009 | Van Rijn et al. | |
| 7,609,922 B2 | 10/2009 | Aoki et al. | |
| 7,653,276 B1 | 1/2010 | Gross et al. | |
| 7,653,279 B1 | 1/2010 | Jacobsen | |
| 7,687,132 B1 | 3/2010 | Gross et al. | |
| 7,901,462 B2 | 3/2011 | Yang et al. | |
| 7,938,989 B1 | 5/2011 | Gross et al. | |
| 8,197,930 B1 * | 6/2012 | Jacobsen et al. ........... | 428/315.5 |
| 2004/0021237 A1 | 2/2004 | Shimizu et al. | |
| 2004/0154252 A1 | 8/2004 | Sypeck et al. | |
| 2004/0200417 A1 | 10/2004 | Hanawa et al. | |
| 2004/0253365 A1 | 12/2004 | Warren et al. | |
| 2004/0264863 A1 | 12/2004 | Suzuki et al. | |
| 2005/0135745 A1 | 6/2005 | Greiner et al. | |
| 2005/0202206 A1 | 9/2005 | Wadley et al. | |

(Continued)

OTHER PUBLICATIONS

U.S. Appl. No. 12/109,262, filed Apr. 24, 2008, entitled "Three-Dimensional Biological Scaffold Comprising Polymer Waveguides," Application, Office Actions, Responses, Notices of Allowance and Cited References.

Kewitsch et al., "Nonlinear Optical Properties of Photoresists for Projection Lithography", Applied Physics Letters, Jan. 22, 1996, 455-457, vol. 68 (No. 4), USA.

Shoji et al., "Optically-Induced Growth of Fiber Patterns into a Photopolymerizable Resin", Applied Physics Letters, Aug. 2, 1999, 737-739, vol. 75 (No. 5), USA.

Kagami et al., "Light-Induced Self-Written Three-Dimensional Optical Waveguide", Applied Physics Letters, Aug. 20, 2001, 1079-1081, vol. 79 (No. 8), USA.

(Continued)

*Primary Examiner* — David M Naff
(74) *Attorney, Agent, or Firm* — Christine Parker & Hale LLP (57) ABSTRACT

A three-dimensional biological scaffold. The scaffold includes at least three sets of polymer waveguides extending along at least three respective directions. The at least three sets of polymer waveguides interpenetrate each other at a plurality of nodes to form a self-supporting structure. In some embodiments, the polymer waveguides may be bio-degradable. In still some embodiments, the three-dimensional biological scaffold may include one or more coating layers for covering surfaces of the polymer waveguides.

7 Claims, 6 Drawing Sheets

(56) References Cited

U.S. PATENT DOCUMENTS

| | | |
|---|---|---|
| 2005/0255289 A1 | 11/2005 | Wadley |
| 2005/0287696 A1 | 12/2005 | Dumais et al. |
| 2006/0029348 A1 | 2/2006 | Kempen et al. |
| 2006/0029349 A1 | 2/2006 | Hoshi et al. |
| 2006/0080835 A1 | 4/2006 | Kooistra et al. |
| 2007/0196066 A1 | 8/2007 | Wang et al. |

OTHER PUBLICATIONS

Bertsch et al., "Microstereolithography: A Review", Materials Research Symposium Proceedings, 2003, 1-13, vol. 758, USA.

Sun et al., "Two-Photon Photo Polymerization and 3D Lithographic Microfabrication", APS, 2004, 169-273, vol. 170, USA.

Chuang et al., "A New Method to Fabricate Polymer Waveguides", Progress in Electromagnetics Research Symposium, Aug. 22-26, 2005, 92-95, Hangzhou, China.

Jang et al., "3D Polymer Microframes That Exploit Length-Scale-Dependent Mechanical Behavior", Advanced Materials, 2006, 2123-2127, vol. 18.

U.S. Appl. No. 11/801,908, filed May 10, 2007, entitled "Three-Dimensional Ordered Open-Cellular Structures", Application and Office Actions.

USPTO Notice of Allowance for related U.S. Appl. No. 11/801,908, filed May 10, 2007, dated Jan. 19, 2012, 17 pages.

\* cited by examiner

THREE-DIMENSIONAL BIOLOGICAL SCAFFOLD AND METHOD OF MAKING THE SAME

CROSS-REFERENCE TO RELATED APPLICATION

This application is a divisional of U.S. patent application Ser. No. 12/109,262, filed on Apr. 24, 2008, now U.S. Pat. No. 8,287,895, entitled "Three-Dimensional Biological Scaffold Comprising Polymer Waveguides," and relates to U.S. patent application Ser. No. 11/580,335, filed on Oct. 13, 2006, now U.S. Pat. No. 7,382,959, entitled "Optically Oriented Three-Dimensional Polymer Microstructures," the entire content of which is incorporated herein by reference.

BACKGROUND OF THE INVENTION

The present invention relates to micro-structures. In particular, the present invention relates to biologically compatible micro-structures and method of making the same.

Scaffold-based biological tissue engineering requires the formation of new tissues which is strongly dependent by the three-dimensional (3D) environment provided by the scaffold. Characteristics of the scaffold that can influence the 3D environment includes its composition, its porous architecture, and its biological response to surrounding tissues/cellular media.

U.S. Pat. No. 6,379,962 (hereinafter the '962 patent) discloses a polymer scaffold having an extensively interconnected macroporous network with macropores having microporous struts as walls. The polymer may be a bio-compatible or bio-degradable polymer. The polymer scaffold is prepared by mixing a liquid polymer with particles, precipitating the liquid polymer with a non-solvent for the liquid polymer and dissolving the particles with a solvent to form the macroporous polymer scaffold. The surface of the polymer scaffold may be modified by acid or base treatment, or by collagen or calcium phosphate deposition. However, this polymer as disclosed in the '962 patent requires surface modification with acid or base treatment or by collagen or calcium phosphate deposition. Furthermore, the structure of the polymer is foam-like with disordered pores that are not homogeneous.

U.S. Pat. No. 6,875,442 (hereinafter the '442 patent) discloses a polymer scaffold with an interconnected macroporous network. The polymer scaffold disclosed embodies macropores having a diameter in a range of 0.5-3.5 mm. The polymer scaffold is prepared using a process which combines the techniques of particulate leaching and phase inversion to render a process that provides amplified means by which to control the morphology of the resulting polymer scaffold. However, the structure disclosed by the '442 patent is foam-like with disordered pores that are not homogeneous.

Similar to the '442 patent, U.S. Pat. No. 7,022,522 (hereinafter the '522 patent) discloses a polymer scaffold that includes an interconnected macroporous network. However, the polymer as disclosed in the '522 patent requires multiple steps to manufacture including particulate leaching and phase inversion. Furthermore, the structure is foam-like with disordered pores that are not homogeneous.

U.S. Pat. No. 6,993,406 (hereinafter the '406 patent) discloses a method for forming a three-dimensional biocompatible porous scaffold structure using a solid freeform fabrication technique that can be used as a medical implant into a living organism. Imaging technology and analysis is first used to determine the three-dimensional design required for the medical implant, such as a bone implant or graft, fashioned as a three-dimensional, biocompatible scaffold structure. The technique is used to either directly produce the three-dimensional porous scaffold structure or to produce an over-sized three-dimensional porous scaffold lattice which can be machined to produce the designed three-dimensional porous scaffold structure for implantation. The method disclosed by the '406 patent, however, requires pre-fabrication software and can manufacture bio-compatible ceramics only.

Therefore, it is desirable to provide an ordered 3D biological scaffold that can be manufactured in simple steps with ordered interconnected pores with controlled pore size. Furthermore, it is desirable to have an ordered 3D biological scaffold that can enable specific cell/tissue growth.

SUMMARY OF THE INVENTION

In accordance with the embodiments of the present invention, different embodiments of a three-dimensional biological scaffold and a method of making the same are provided.

In one embodiment according to the present invention, a three-dimensional (3D) biological scaffold is provided. The 3D biological scaffold includes at least three sets of bio-degradable polymer waveguides extending along at least three respective directions. The at least three sets of bio-degradable polymer waveguides interpenetrate each other at a plurality of nodes to form a self-supporting structure having a plurality of ordered interconnected pores. The plurality of ordered interconnected pores are sized to facilitate ingress of at least one of biological cells, vascular tissue, or nutrient media.

The plurality of ordered interconnected pores may can sized to about 100-300 µm for trabecular bone implants. A bio-degradable polymer waveguide of the at least three sets of bio-degradable polymer waveguides may have a cross-sectional diameter about 1 µm to about 1 mm. The plurality of ordered interconnected pores may occupy a free space of not less than about 40% by volume and not greater than about 99% by volume of the self-supporting structure. The at least three sets of bio-degradable polymer waveguides may include a bio-degradable polymer selected from one of starches, starch-similar polymers, starch-synthetic blend polymers, esters, amides, anhydrides, urethanes, ureas, carbonates, or saccharides. Surfaces of the three-dimensional biological scaffold may be treated to facilitate cellular recognition and proliferation with a material that has affinity for one of polymeric, ceramic, or metallic surfaces. The material may include one of a silane, a bi-phasic calcium phosphate, a bone morphogenetic protein, a polysaccharide, a biochemical agent, or a mineral precursor.

In another embodiment, a three-dimensional biological scaffold is provided. The three-dimensional biological scaffold includes at least three sets of polymer waveguides extending along at least three respective directions. Surfaces of the at least three sets of polymer waveguides are coated with one or more coating layers. The at least three sets of polymer waveguides interpenetrate each other at a plurality of nodes to form a self-supporting structure having a plurality of ordered interconnected pores. The plurality of ordered interconnected pores are sized to facilitate ingress of at least one of biological cells, vascular tissue, or nutrient media.

The plurality of ordered interconnected pores may be sized to about 250 µm. The one or more coating layers may include one of metal or ceramic. The one or more coating layers may include a material selected from one of titanium (Ti), nickel (Ni), Ti6Al4V, or nickel alloy. The one or more coating layers may include a material selected from one of silicon carbide (SiC), silicon nitride (Si3N4), hafnium carbide (HfC), chromium carbide (Cr3C2), boron nitride (B4N), cubic boron nitride (c-BN), hexagonal boron nitride (h-BN), boron carbide (B4C), aluminum oxide (Al2O3), titanium diboride (TiB2), titanium nitride (TiN), or zirconium dioxide (ZrO2). A polymer waveguide of the at least three sets of polymer waveguides may have a cross-sectional diameter from about 1 μm to about 1 mm. The polymer waveguide may have a cross-sectional diameter from about 100 μm to about 500 μm. The plurality of ordered interconnected pores may occupy a free space of not less than about 40% by volume and not greater than about 99% by volume of the self-supporting structure. The free space may be not less than about 70% by volume and not greater than about 90% by volume of the self-supporting structure. Surfaces of the three-dimensional biological scaffold may be treated to facilitate cellular recognition and proliferation with a material that has affinity for one of polymeric, ceramic, or metallic surfaces. The material may include one of a silane, a bi-phasic calcium phosphate, a bone morphogenetic protein, a polysaccharide, a biochemical agent, or a mineral precursor.

In still another embodiment, a method for forming a three-dimensional biological scaffold is provided. A volume of photo-monomer is secured. A mask having a plurality of apertures is placed between at least one collimated light source and the volume of photo-monomer. A plurality of collimated light beams from the at least one collimated light source is directed through the plurality of apertures into a portion of the volume of photo-monomer to polymerize the portion to form a plurality of bio-degradable polymer waveguides. And, photo-monomer of the volume of photo-monomer not polymerized is removed to leave behind the three-dimensional biological scaffold having a plurality of ordered interconnected pores. At least three of the plurality of bio-degradable polymer waveguides intersect each other at an aperture of the plurality of apertures. The quantity and opening sizes of the plurality of apertures are selected to adjust the quantity and dimensions of the plurality of ordered interconnected pores to facilitate ingress of at least one of biological cells, vascular tissue, or nutrient media. The plurality of ordered interconnected pores may occupy a free space of not less than about 40% by volume and not greater than about 99% by volume of the three-dimensional biological scaffold.

In yet another embodiment, a method for forming a three-dimensional biological scaffold is provided. A volume of photo-monomer is secured. A mask having a plurality of apertures is placed between at least one collimated light source and the volume of photo-monomer. A plurality of collimated light beams from the at least one collimated light source is directed through the plurality of apertures into a portion of the volume of photo-monomer to polymerize the portion to form a plurality of polymer waveguides. Photo-monomer of the volume of photo-monomer not polymerized is removed to leave behind the three-dimensional biological scaffold having a plurality of ordered interconnected pores. And, surfaces of the plurality of polymer waveguides are covered with one or more coating layers. At least three of the plurality of polymer waveguides intersect each other at an aperture of the plurality of apertures. The quantity and opening sizes of the plurality of apertures are selected to adjust the quantity and dimensions of the plurality of ordered interconnected pores to facilitate ingress of at least one of biological cells, vascular tissue, or nutrient media.

The plurality of ordered interconnected pores may occupy a free space of not less than about 40% by volume and not greater than about 99% by volume of the three-dimensional biological scaffold. The one or more coating layers may include metal, and the one or more coating layers may include ceramic.

DETAILED DESCRIPTION

The present invention will now be described more fully hereinafter with reference to the accompanying drawings, in which exemplary embodiments of the invention are shown. The dimensions of layers and other elements shown in the accompanying drawings may be exaggerated to more clearly show details. The present invention should not be construed as being limited to the dimensional relations shown in the drawings, nor should the individual elements shown in the drawings be construed to be limited to the dimensions shown.

Embodiments of the present invention provide a 3D biological scaffold, defined by a microtruss structure made of a polymeric, ceramic or metallic material, that has application in biological systems. The 3D biological scaffold may be made solely of a polymer (e.g., bio-degradable or other), ceramic, metal, or any combination thereof with the microtruss structure. An optically templated polymer scaffold determines the final shape and dimensions of the 3D biological scaffold which has the proper pore size and surface chemistry to provides an optimal environment for vascular, cellular, and biomineral growth/remodeling.

An ideal 3D biological scaffold should have appropriate mechanical properties, adequate degradation rate, porosity, interconnectivity, and permeability to allow ingress of cells, vascular tissue, and other nutrient media. The diameter of the pores of the 3D biological scaffold should be at least 100 micron and not larger than 300 micron to enable cell penetration into the structure, to allow tissue ingrowths and to allow blood supply and nutrient to get into the scaffold. For example, the pore size of the 3D biological scaffold may be sized to 250 micron to facilitate trabecular bone implant application. In addition, having the proper surface chemistry is required to enhance cell recognition, attachment, and proliferation. A simple polymerization scheme allows for a controllable, reproducible polymeric structure having a 3D porous network with controlled porosity and surface chemistry. Unlike other known scaffolds in the art, which lack an interconnected porous network, embodiments of the present invention provide an ordered 3D structure with optimized characteristics, for example, pore scale and interconnectivity, for a particular biological system based on cell diameter, chemistry and other factors.

The present invention has applications in many areas. For example, the medical, dental, and orthopedic communities need biologically compatible structures that provide ideal templating, porosity and interconnectivity for cell, bone, and tooth growth. Embodiments of the present invention can enable polymeric, ceramic, and metallic structures that are ideal or highly compatible for tissue engineering.

Embodiments of the present invention are based on a 3D polymer scaffold. The techniques of making the 3D polymer scaffold are disclosed in a related U.S. patent application Ser. No. 11/580,335 (hereinafter the '335 application) entitled "Optically Oriented Three-Dimensional Polymer Microstructures," which is incorporated herein by reference in its entirety. The '335 application discloses a method and system of fabricating porous cellular polymer materials with an ordered 3D microstructure using a simple technique. These cellular materials are created from a pattern of self-propagating polymer waveguides, which are formed in an appropriate photopolymer. More detail of the techniques can be found in the '335 application.

In reference to the '335 application, a fixed light input (e.g., collimated UV light) is used to cure (i.e., polymerize) polymer optical waveguides, which can self-propagate in a 3D pattern. The propagated polymer optical waveguides form an ordered 3D microstructure that can be polymerized without anything moving during the formation process to provide a path to large scale, inexpensive production.

Some liquid polymers, referred to as photopolymers, undergo a refractive index change during the polymerization process. The refractive index change can lead to a formation of polymer optical waveguides. If a monomer that is photosensitive is exposed to light (e.g., typically UV) under the right conditions, the initial area of polymerization, such as a small circular area, will "trap" the light and guide it to the tip of the polymerized region, further advancing that polymerized region. This process will continue, leading to the formation of a waveguide structure with approximately the same cross-sectional dimensions along its entire length.

The '335 application discloses a polymer cellular material with an ordered 3D microstructure by creating a pattern of self-propagating optical waveguides in an appropriate photopolymer. A formation of a single and multiple polymer waveguides will be described in more detail below, followed by a more detailed description on how to pattern these polymer waveguides to form an ordered 3D microstructure.

Formation of a Single Polymer Waveguide with Single Aperture

Figure 1:
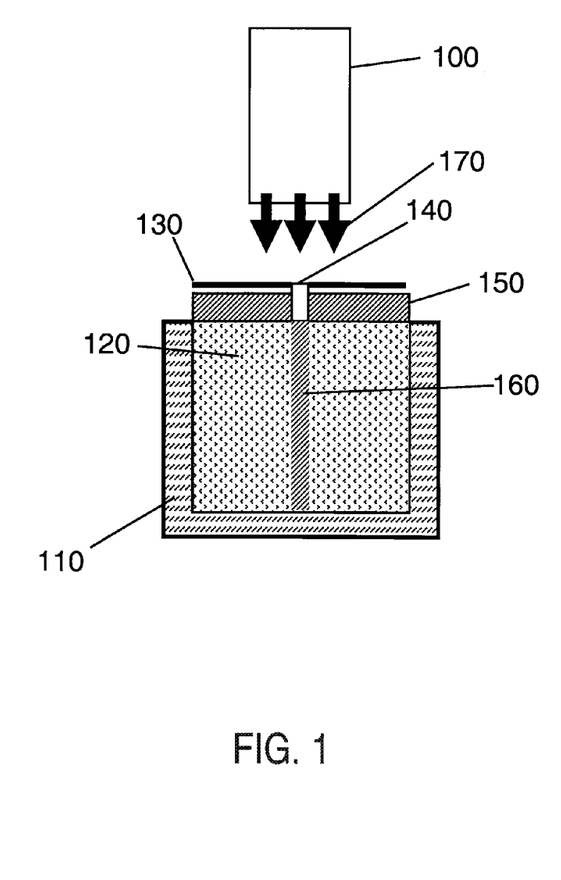
FIG. 1 is a schematic diagram of a system to form a single waveguide from a single collimated beam through a single aperture pursuant to aspects of the present invention.

Referring to FIG. 1, a system to form a single optical waveguide includes a collimated light source 100, a reservoir 110 (e.g., a mold) having a volume of monomer 120 that will polymerize at a wavelength of a collimated light beam 170 provided by the light source 100, and a patterning apparatus, such as a mask 130 with a single aperture 140 (e.g., an open area) of a given shape and dimension.

The single collimated beam 170 is directed through the aperture 140 in the mask 130 to the monomer 120. Between the mask 130 and the monomer 120, there may be a substrate 150. The substrate can be composed of a material, such as glass, Mylar, and other suitable materials that will transmit the incident light beam to the monomer 120. That is, in one embodiment of the present invention, the substrate 150 is substantially transparent to the incident light beam. On the surface of the monomer 120, in the area exposed to a portion of the light beam, an optical waveguide 160 will begin to polymerize.

The index of refraction change between the polymer and monomer will "trap" and "focus" the light in the polymer and guide the polymerization process. Due to this self-guiding/self-focusing effect, the polymerized waveguide 160 will form with an approximately constant cross-section and a length much greater than the cross-sectional dimensions. The direction in which this polymer waveguide 160 will grow is dependent on the direction of the incident beam. The cross-section of the polymer waveguide 160 is dependent on the shape and dimensions of the incident collimated beam, which in turn is dependent on the shape and dimensions of the aperture 140 in the mask 130. The length to which the polymer waveguide 160 can "grow" is dependent on a number of parameters including the size, intensity, and exposure time of the incident beam, as well as the light absorption/transmission properties of the photopolymer. The time in which it takes to form a polymer waveguide depends on the kinetics of the polymerization process.

To put it another way, when the portion of the collimated light beam passes through the mask 130 and first hits the liquid photo-monomer 120, a polymer "tip" is formed. There is a large enough difference between the refractive index of the monomer and the polymer to cause internal reflection of the light in the polymer—this is the same principle as when light travels through fiber optics. Because of this internal reflection effect, the light is essentially focused to the tip of the polymer, causing the monomer at the tip to cure (i.e., polymerize). This will also propagate the tip of the polymer through the liquid monomer 120, forming the self-propagating polymer optical waveguide 160. In addition, because of this internal reflection affect, the waveguide 160 can be "very" long with respect to the cross-sectional dimensions, all while maintaining a constant cross-section through its length. Eventually the formation of the polymer waveguide 160 will stop at the end of the monomer reservoir 110, or it will stop prior to that if there is not enough energy to polymerize the monomer 120. This happens because the polymer itself will absorb some of the portion of the collimated light beam passing through the mask 130.

Formation of Multiple Polymer Waveguides with Single Aperture

As mentioned above, the direction in which the polymer waveguide will form is dependent on the angle of the incident collimated beam. If the collimated beam is perpendicular to a flat monomer surface (as shown in FIG. 1), the polymer waveguide will propagate, or grow perpendicular to the monomer surface. By contrast, referring to FIG. 2, if the incident collimated beam is directed at an angle, the polymer waveguide will grow at an angle relative to the monomer surface. Note this angle will be affected by the change in refractive index between the air and/or substrate and the monomer due to refraction.

Figure 2:
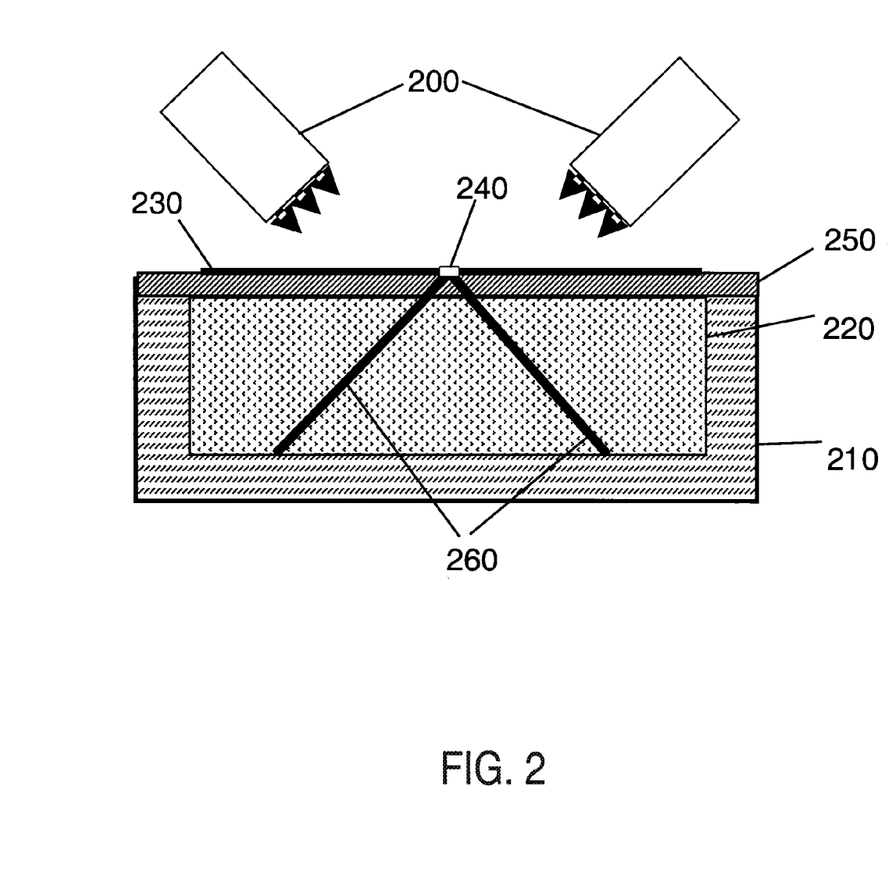
FIG. 2 is a schematic diagram of a system to form multiple waveguides from a single collimated beam or multiple collimated beams through a single aperture pursuant to aspects of the present invention.

That is, as shown in FIG. 2, a system to form multiple optical waveguides 260 includes one or more collimated light sources 200, a reservoir 210 (e.g., mold) having a volume of monomer 220 that will polymerize at a wavelength of collimated light beams provided by the light sources 200, and a patterning apparatus, such as a mask 230 with a single aperture (e.g., open area) 240 of a given shape and dimension. Between the mask 230 and the monomer 220, there may be a substrate 250.

Through the single aperture 240 as described above, the multiple waveguides 260 can be formed by directing multiple collimated beams at different angles through the aperture 240. That is, in one embodiment of the invention, a single collimated light source is used. Multiple waveguides are formed from a plurality of exposures of the collimated light beam of the single collimated light source with a mask having a single aperture, and the single collimated light source is adapted to move with respect to the mask between each of the exposures.

Alternatively, the multiple waveguides 260 can be formed one at a time through the single aperture 240 by simply changing the incident angle of a single collimated beam after the formation of each of the waveguides 240. That is, in another embodiment of the present invention, multiple collimated light sources are adapted to produce and direct multiple collimated light beams at different angles with respect to a point of a mask having a single aperture. Multiple waveguides are formed from a single exposure of the multiple light beams of the multiple collimated light sources with the mask having the single aperture.

Formation of 3D Microstructure using Patterned Optical Waveguides

The technique to create a 3D polymer microstructure is based on the above described approach for forming multiple optical waveguides with a single aperture. However, instead of using a mask with a single aperture, a mask with a two-dimensional pattern of apertures is used to create a three-dimensional polymer microstructure as is shown in FIG. 3.

Figure 3:
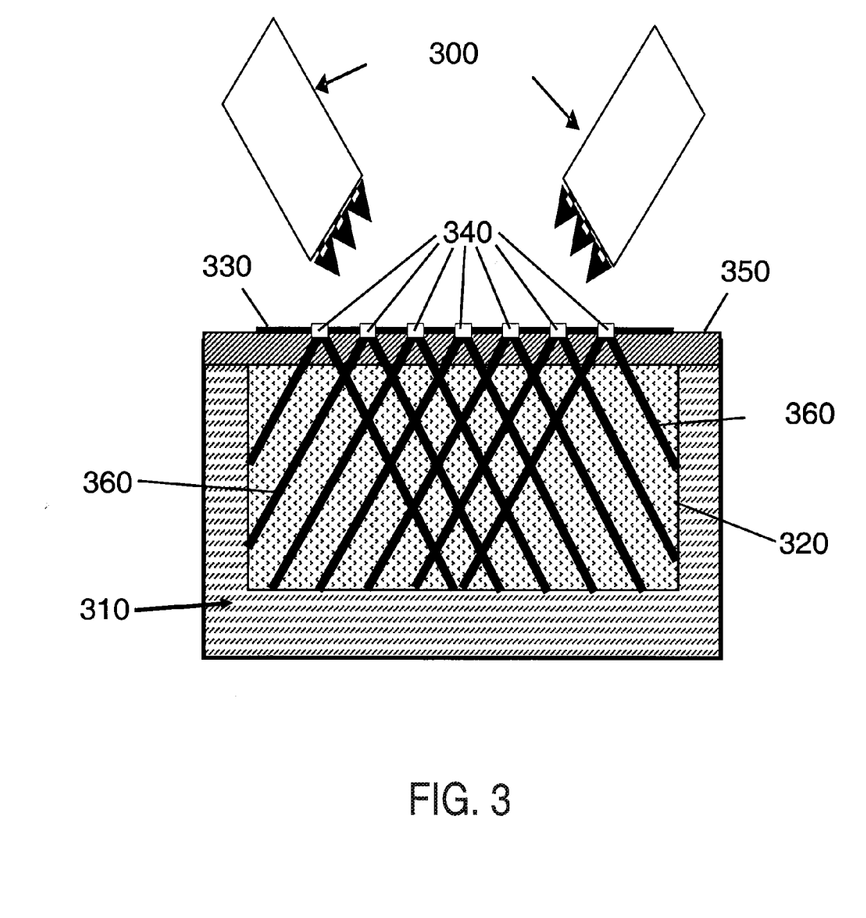
FIG. 3 is a schematic diagram of a system to form a 3D structure (e.g., a 3D ordered polymer microstructure) formed from multiple waveguides created using a single collimated beam or multiple collimated beams through multiple apertures pursuant to aspects of the present invention.
Figure 4A:
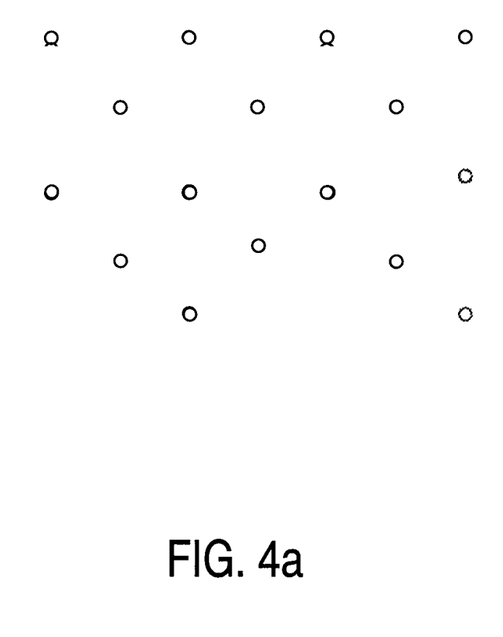
FIG. 4a illustrates an example of a square mask pattern (or a square mask aperture pattern) pursuant to aspects of the present invention.
Figure 4B:
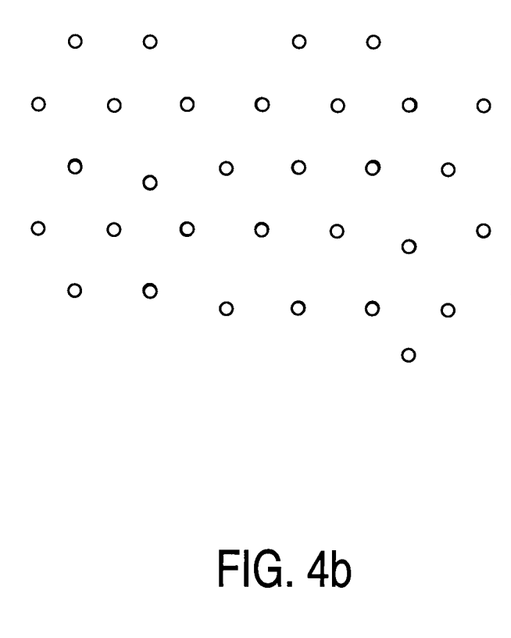
FIG. 4b illustrates an example of a hexagonal mask pattern (or a hexagonal mask aperture pattern) pursuant to aspects of the present invention.

Referring to FIG. 3, a system to form a 3D polymer microstructure includes one or more collimated light sources 300, a reservoir (e.g., a mold) 310 having a volume of monomer 320 that will polymerize at a wavelength of collimated light beams provided by the light sources 300, and a patterning apparatus, such as a mask 330 with multiple apertures (e.g., open areas) 340. Each of the apertures 340 has a given shape and dimension substantially matching a cross section geometry of a polymer waveguide 360. Between the mask 330 and the monomer 320, there may be a substrate 350. Here, in FIG. 3, a truly 3D network can be formed because the intersecting polymer waveguides 360 will simply polymerize together, but will not interfere with waveguide propagation. Also, the spacing between the plurality of waveguides 360 corresponds with the pattern of the plurality of apertures 340. The pattern of the apertures 340 may, for example, be in a square pattern as shown in FIG. 4a and/or in a hexagonal pattern as shown in FIG. 4b. The hole (i.e., aperture) spacing, i.e., distance between apertures 340 in the mask 330, and the number of waveguides 360 formed from each of the apertures 340 will determine the open volume fraction (i.e., open space) of the formed 3D microstructure. It should be appreciated by a person skilled in the art that once a certain pore size is determined for a particular application, the hole spacing and the size of the aperture can be adjusted accordingly to produce the desired pore size.

Figure 5:
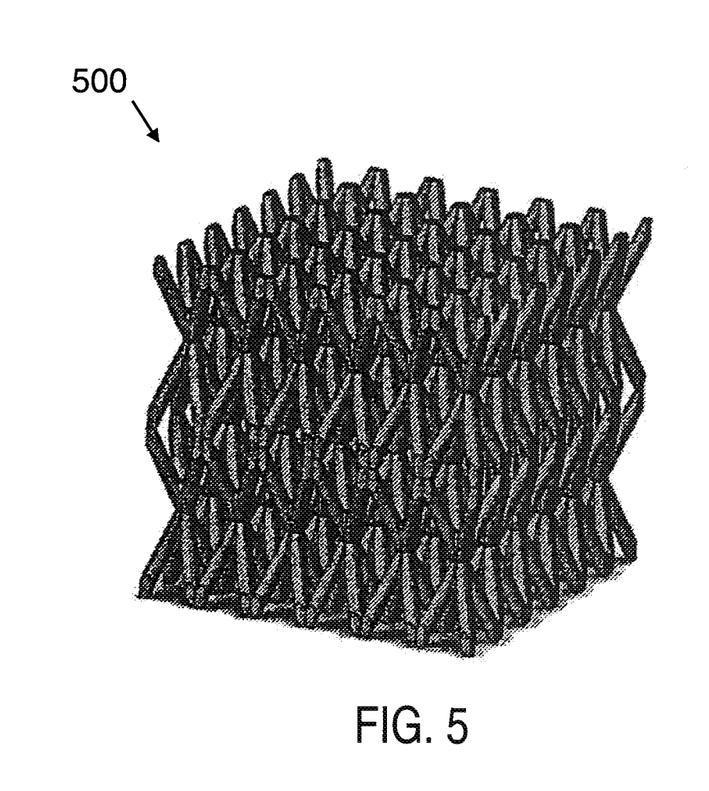
FIG. 5 illustrates an example of a 3D polymer scaffold pursuant to aspects of the present invention.

As such, through the process shown in FIG. 3, an exemplary 3D polymer scaffold 500 (e.g., a 3D ordered polymer microstructure) can be designed and provided as shown in FIG. 5. The design parameters include: 1) the angle and pattern of the polymer waveguides with respect to one another; 2) the packing, or relative density of the resulting cellular structure (or the open volume fraction); and 3) the cross-sectional shape and dimensions of the polymer waveguides. By varying these design parameters, the exemplary 3D polymer scaffold 500 can be adapted to facilitate a particular implant application. By way of example, in human trabecular bone implant application, the pore size of the scaffold can be within the range of 0.5 to 3.5 mm to match the pore size of human trabecular bone. The high level of interconnectivity of the pores of the 3D polymer scaffold 500 enhances both penetration of the scaffold 500 by cells and nutrient flow to the cells.

In one embodiment according to the present invention, the 3D polymer scaffold 500 includes bio-degradable polymer such as, but not limited to, starches, starch-similar polymers, starch-synthetic blend polymers, esters, amides, anhydrides, urethanes, ureas, carbonates, or saccharides.

In another embodiment according to the present invention, the truss elements (i.e., the waveguides 360) may have diameters between about 1 µm and about 1 mm, and the 3D polymer scaffold can has between 40% and 99% of interconnected free space.

Figure 6:
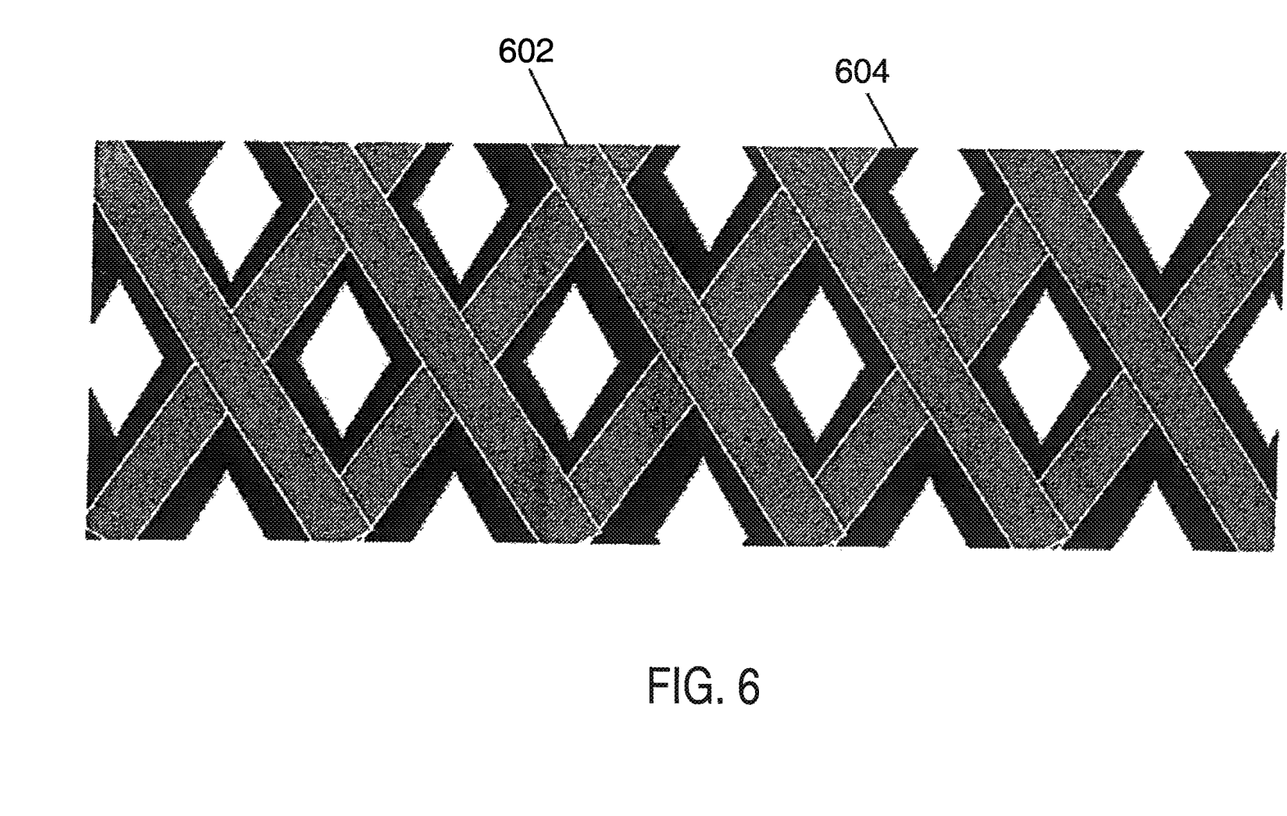
FIG. 6 illustrates a cross-sectional view of another example of a 3D polymer scaffold pursuant to aspects of the present invention.

In still another embodiment according to the present invention, the 3D polymer scaffold 602 can be deposited with one or more layers of material 604 as shown in FIG. 6. The layers of material can be, but not limited to, ceramic or metal. Exemplary ceramic can be, but not limited to, one of silicon carbide (SiC), silicon nitride (Si3N4), hafnium carbide (HfC), chromium carbide (Cr3C2), boron nitride (B4N), cubic boron nitride (c-BN), hexagonal boron nitride (h-BN), boron carbide (B4C), aluminum oxide (Al2O3), titanium diboride (TiB2), titanium nitride (TiN), or zirconium dioxide (ZrO2). Exemplary metal can be, but not limited to, one of titanium (Ti), nickel (Ni), Ti6Al4V, or nickel alloy. The layers of material can be applied by chemical vapor deposition, reacting the 3D polymer scaffold with a gas or liquid phase reactant, or coating the 3D polymer scaffold with a suitable pre-ceramic polymer.

In yet another embodiment according to the present invention, the 3D polymer scaffold's surface is treated to enable specific functionalities, such as specific cellular recognition and proliferation needed to stimulate cell growth and achieve bio-compatibility. By immersing a ceramic or metal coated 3D polymer scaffold in a solution bath of various mono- or multi-functional molecules (e.g., biochemical agents or mineral precursor), a biologically specific surface can be produced. The functional molecules can have an affinity for polymeric, ceramic, or metallic surfaces. This treated 3D polymer scaffold can provide bone-implant scaffolds absorption/recognition sites for molecular/cellular species such as bone morphogenetic proteins and bi-phasic calcium phosphate that are critical to osteogenesis. These molecules/minerals are critical during osteoinduction (i.e., allows for cell differentiation and bone morphogenesis). In addition, pore size and surface functionality are critical during osteogenesis (i.e., forming bone), whereby proper adsorption sites and transportation pathways are provided by the 3D scaffold to the bone-mineralizing cells (i.e., osteoblasts). Cell transport is also critical during remodeling of bone; that is, it is necessary to transport bone-resorbing cells (i.e., osteoclasts) to growing/remodeled bone.

Although certain exemplary embodiments of the present invention have been disclosed for illustrative purposes, those skilled in the art would appreciate that various modifications, additions and subtractions are possible, without departing from the scope and spirit of the present invention as disclosed in the accompanying claims and their equivalents.

What is claimed is:
1. A method for forming a three-dimensional biological scaffold having a plurality of ordered interconnected pores, the method comprising:
 placing a mask having a plurality of apertures between at least one collimated light source and a volume of photo-monomer, in a first position relative to the volume of photo-monomer;

directing a plurality of collimated light beams from the at least one collimated light source through the plurality of apertures into a portion of the volume of photo-monomer, while the mask remains in the first position relative to the volume of photo-monomer, to polymerize the portion to form a plurality of bio-degradable polymer waveguides; and removing photo-monomer of the volume of photo-monomer not polymerized to leave behind the three-dimensional biological scaffold having a plurality of ordered interconnected pores, wherein at least three of the plurality of bio-degradable polymer waveguides interpenetrate each other at an aperture of the plurality of apertures, and wherein the quantity and opening sizes of the plurality of apertures are selected to adjust the quantity and dimensions of the plurality of ordered interconnected pores to facilitate ingress of at least one of biological cells, vascular tissue, or nutrient media.

2. The method of claim 1, wherein the plurality of ordered interconnected pores occupy a free space of not less than about 40% by volume and not greater than about 99% by volume of the three-dimensional biological scaffold.

3. The method of claim 1, wherein the plurality of ordered interconnected pores are sized to about 100 μm to 300 μm.

4. A method for forming a three-dimensional biological scaffold having a plurality of ordered interconnected pores, the method comprising:

placing a mask having a plurality of apertures between at least one collimated light source and a volume of photo-monomer, in a first position relative to the volume of photo-monomer;

directing a plurality of collimated light beams from the at least one collimated light source through the plurality of apertures into a portion of the volume of photo-monomer, while the mask remains in the first position relative to the volume of photo-monomer, to polymerize the portion to form a plurality of polymer waveguides;

removing photo-monomer of the volume of photo-monomer not polymerized to leave behind the three-dimensional biological scaffold having a plurality of ordered interconnected pores; and covering surfaces of the plurality of polymer waveguides with at least one coating layer, wherein at least three of the plurality of polymer waveguides interpenetrate each other at an aperture of the plurality of apertures, and wherein the quantity and opening sizes of the plurality of apertures are selected to adjust the quantity and dimensions of the plurality of ordered interconnected pores to facilitate ingress of at least one of biological cells, vascular tissue, or nutrient media.

5. The method of claim 4, wherein the plurality of ordered interconnected pores occupy a free space of not less than about 40% by volume and not greater than about 99% by volume of the three-dimensional biological scaffold.

6. The method of claim 4, wherein the plurality of ordered interconnected pores are sized to about 100 μm to 300 μm.

7. The method of claim 4, wherein the at least one coating layer comprises one of metal or ceramic.

\* \* \* \* \*